United States Patent [19]

Markley et al.

[11] Patent Number: 4,935,436
[45] Date of Patent: Jun. 19, 1990

[54] SUBSTITUTED TRIAZOLES AND THEIR USE AS FUNGICIDES

[75] Inventors: Lowell D. Markley; Richard B. Rogers, both of Midland, Mich.; Neil V. Kirby; John W. Liebeschuetz, both of Wantage, Great Britain; Peter F. S. Street, Burbage, Great Britain

[73] Assignee: The Dow Chemical Company, Midland, Mich.

[21] Appl. No.: 299,910

[22] Filed: Jan. 23, 1989

[51] Int. Cl.$^5$ .................. A01N 43/653; C07D 249/08
[52] U.S. Cl. ..................................... 514/383; 514/184; 548/101; 548/267.4; 548/267.6; 548/267.8; 548/268.6
[58] Field of Search ................ 548/101, 262; 514/184, 514/383

[56] References Cited

U.S. PATENT DOCUMENTS 4,551,469 11/1985 Parry et al. .................... 514/383
4,616,027 10/1986 Richardson et al. .............. 514/383

OTHER PUBLICATIONS

ICI, "Preparation of 2,2-dimethyl-3-hydroxy, etc.", CA 106:176401c.

Primary Examiner—Glennon H. Hollrah
Assistant Examiner—Patricia L. Morris
Attorney, Agent, or Firm—S. Preston Jones; Ronald G. Brookens

[57] ABSTRACT

Substituted triazole compounds, their preparation, compositions containing said compounds and the use of said compositions to control fungal infections in plants are disclosed.

68 Claims, No Drawings

SUBSTITUTED TRIAZOLES AND THEIR USE AS FUNGICIDES

FIELD OF THE INVENTION

The present invention is directed to substituted triazole compounds, compositions containing said compounds and the use of said compositions to control fungal infections in plants.

SUMMARY OF THE INVENTION

The present invention is directed to substituted triazole compounds corresponding to the formulae

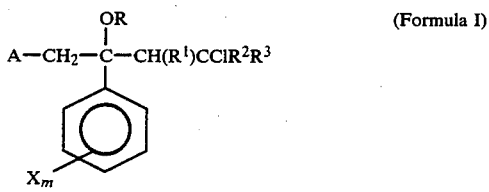

wherein
A represents

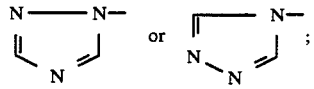

R represents —H, or —C(O)R$^4$;
R$^1$ and R$^2$ each independently represent —H, halo, C$_1$-C$_4$ straight chain alkyl;
R$^3$ represents —H, halo, C$_1$-C$_4$ alkyl, C$_1$-C$_4$-haloalkyl, CN, or —C(O)NR$^5$R$^6$;
R$^4$ represents C$_1$-C$_4$ alkyl, C$_1$-C$_2$ haloalkyl, phenyl or substituted phenyl;
R$^5$ and R$^6$ each independently represent —H, —CN, C$_1$-C$_4$ alkyl, C$_3$-C$_8$ cycloalkyl, aryl or aralkyl;
each X independently represents —H, halo, —CN, C$_1$-C$_4$ alkyl, C$_1$-C$_4$ haloalkyl, C$_1$-C$_4$ alkoxy, C$_1$-C$_4$ alkoxy, nitro, phenyl or benzyloxy;
m represents 1 to 3; and
the acid addition salts and metal complexes thereof, with the proviso that when m is greater than 1, X is only in the 2, 3, 4 or 5 ring positions.

In addition, the present invention is directed to compositions containing compounds of Formula I, as an active ingredient therein, and to methods of using said compositions in the kill and control of plant fungal organisms.

In the present specification and claims, the term "straight chain alkyl" designates alkyl groups such as methyl, ethyl, propyl or butyl.

In the present specification and claims, the term "halo" designates bromo, chloro or fluoro atoms.

In the present specification and claims, the term "haloalkyl" designates an alkyl group as defined above which is substituted with from at least one (1) bromo, chloro or fluoro atom up to perbromo-, perchloro or perfluoro substituents including mixtures thereof, such as, for example, chloromethyl, dichloromethyl, trichloromethyl, 1-chloroethyl, 1-chloro-n-propyl, perfluoro-n-butyl and the like.

The term "cycloalkyl" is employed herein to mean an alkyl moiety characterized by one or more closed rings and containing from 3 to about 8 carbon atoms, such as, for example, cyclopropyl, cyclobutyl, cyclopentyl, cyclohexyl, cycloheptyl, cyclooctyl and the like.

The term "substituted phenyl" includes, but is not limited to, a phenyl group substituted with from 1 to 5 C$_1$-C$_6$ alkyl groups, such as, for example, methylphenyl, dimethylphenyl, trimethylphenyl, ethylphenyl, diethylphenyl, triethylphenyl, methylethylphenyl, dimethylethylphenyl, propylphenyl, butylphenyl, pentylphenyl, hexylphenyl or halo groups, such as, for example, mono, di, tri, tetra or pentahalophenyl.

The term "aralkyl" designates an aryl moiety bonded to a C$_1$-C$_6$ alkyl moiety, such as, for example, phenylmethyl, diphenylmethyl, triphenylmethyl, phenylethyl, diphenylethyl, triphenylethyl, phenylpropyl, phenylbutyl, phenylpentyl, phenylhexyl and the like.

The active ingredients of Formula I wherein R represents —H or —C(O)R$^4$, R$^1$ is —H, R$^2$ is halo, R$^3$ is halo or haloalkyl, R$^4$ is alkyl or haloalkyl, each X is independently —H, halo, alkyl, haloalkyl or phenyl, and m is greater than 1, constitutes a preferred embodiment. The active ingredients of Formula I, wherein m is 0, 1 or 2, constitutes a more preferred embodiment. The active ingredients of Formula I wherein R represents —H or —C(O)R$^4$, R$^1$ is —H, R$^2$ is chloro, R$^3$ is chloro or trifluoromethyl, R$^4$ is methyl or trifluoromethyl and X is —H, halo, methyl, trifluoromethyl or phenyl constitutes a most preferred embodiment.

In the present invention, it is to be noted that all substituent groups are sterically compatible with each other. The term "sterically compatible" is employed to designate substituent groups which are not affected by steric hindrance as this term is defined in *The Condensed Chemical Dictionary*, 7th edition, Reinhold Publishing Co., N.Y. page 893 (1966) which definition is as follows:

"steric hindrance. A characteristic of molecular structure in which the molecules have a spatial arrangement of their atoms such that a given reaction with another molecule is prevented or retarded in rate".

Sterically compatible may be further defined as reacting compounds having substituents whose physical bulk does not require confinement within volumes insufficient for the exercise of their normal behavior as discussed in *Organic Chemistry* of D. J. Cram and G. Hammon, 2nd edition, McGraw-Hill Book Company, N.Y., page 215 (1964).

The compounds of the present invention contain to asymmetrical active centers designated by "*"

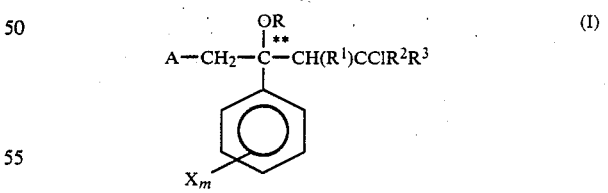

when R$^1$ is other than hydrogen and can exist in optically active stereoisomeric forms such as the R and S enantiomeric forms. The use of the various mixtures and racemates of the above isomers are within the scope of the present invention. Additionally, one of the enantiomers of such compounds may be found to be more active biologically than the other enantiomer and the more active enantiomer, isolated by conventional procedures, may be used whenever the greater activity justifies any extra expenses which may occur from the preparation of said isomer.

The above indicated isomers can be resolved employing conventional separation techniques known to those skilled in the art.

A general discussion of the isomer activity difference phenomenon can be found in A. Albert, *Selective Toxicity*, 4th edition, Met Luen & Co., Ltd., London, 1968, pp. 387–390 and more particular discussions in A. Fredga and B. Åberg, "Stereoisomerism in plant growth regulators of the auxin type", Ann. Rev. Plant Physiology 16: 53–72, 1965, and in E. J. Lien et al, "Quantitative structure-activity correlation of optical isomers", Molecular Pharmacology 12: 598–604, 1976.

The compounds of the present invention are generally crystalline solids at ambient temperatures which are soluble in many organic solvents.

The acid addition salts can be salts of an inorganic or organic acid, all the organic and inorganic acids which form stable physiologically acceptable salts are suitable for salt formation with compounds of the Formula I. Examples of salts are chlorides, bromides, iodides, sulfates, phosphates, acetates, oxalates, fumarates, malonates, alkylsulfonates, arylsulfonates, alkylarylsulfonates, octanoates and oleates.

The metal complexes have the formula $$[M[X]n]Ap.zH_2O \qquad (II)$$

wherein

M represents copper, zinc, manganese or iron;

X represents compound of Formula I;

A represents an anion (e.g. chloride, bromide, iodide, nitrate, sulfate or phosphate anion);

n represents the integer 2 or 4;

p is an integer which corresponds to the valence of M; and z represents an integer of from 0 to 12.

Representative compounds which correspond to Formula I include the compounds set forth below in Table I.

TABLE I $$\text{A—CH}_2\text{—}\underset{\underset{\text{C}_6\text{H}_4\text{X}_m}{|}}{\overset{\overset{\text{OR}}{|}}{\text{C}}}\text{—CH(R}^1\text{)CClR}^2\text{R}^3 \qquad (I)$$

| A | R | R¹ | R² | R³ | Xₘ |
|---|---|---|---|---|---|
| 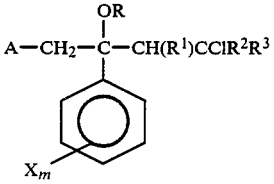 N——N—<br>‖ ⟍⫽<br> N | H | H | H | Cl | H |
| " | H | H | Cl | Cl | 3,5-Cl₂ |
| " | H | H | H | Br | 3,5-Br₂ |
| " | H | Br | Br | Br | H |
| " | H | Cl | Cl | Cl | 3,5-(CF₃)₂ |
| " | H | H | Cl | Cl | 4-CF₃ |
| " | H | H | H | F | 4-CF₂Cl |
| " | H | H | Cl | CF₃ | 4-Cl |
| " | H | CH₃ | CH₃ | C(O)NH₂ | 4-Cl |
| " | H | C₄H₉ | C₄H₉ | CCl₂CCl₃ | 4-Cl |
| " | H | H | Cl | Cl | 2,4-F₂ |
| " | H | H | Cl | CH₃ | 4-Cl |
| 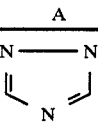 ⌐——N—<br>‖ ⫽<br>N⟍N | H | H | Cl | Cl | 2,4-Cl₂ |
|  N——N—<br>‖ ⫽<br> N | C(O)CF₃ | H | Cl | Cl | 4-Cl |
| " | H | H | Cl | Cl | 4-Cl |
| " | H | H | Cl | Cl | 4-F |
| " | H | H | Cl | Cl | 4-Br |
|  ⌐——N—<br>‖ ⫽<br>N⟍N | H | H | Cl | Cl | 3,5-Cl₂ |
|  N——N—<br>‖ ⫽<br> N | H | H | Cl | Cl | 2,4-Cl₂ |
| " | H | H | Cl | Cl | 4-t-C₄H₉ |
| " | H | H | Cl | Cl | H |
| " | H | H | Cl | Cl | 4-phenyl |
| " | H | H | Cl | Cl | 4-CH₃ |

TABLE I-continued

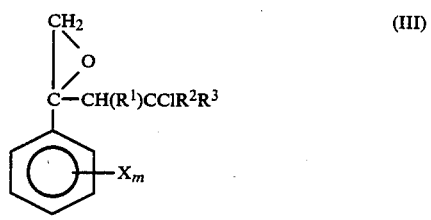

| A | R | $R^1$ | $R^2$ | $R^3$ | $X_m$ |
|---|---|---|---|---|---|
| " | C(O)CH$_3$ | H | Cl | Cl | 4-Cl |
| " | C(O)C$_4$H$_9$ | C$_2$H$_5$ | C$_2$H$_5$ | CN | 3,5-(CH$_3$)$_2$ |

The compounds of the present invention can be prepared by a variety of methods. The compounds wherein R is hydrogen can be prepared by the reaction of an appropriate oxirane reactant, corresponding to Formula III:

$$\begin{array}{c} CH_2 \\ \diagdown \\ O \\ \diagup \\ C-CH(R^1)CClR^2R^3 \\ | \\ \text{Ph}-X_m \end{array} \quad (III)$$

where X and m are as defined hereinabove, with 1,2,4-triazole in the presence of acetic acid at a temperature of from about 75° about 110° C. When this preparative procedure is employed, both the asymmetrical and symmetrical triazole isomer products are obtained. If desired, these two products can be separated from each other employing conventional separation techniques, such as, for example, high pressure liquid chromatography.

In another procedure for preparing compounds wherein R is hydrogen, the appropriate oxirane reactant of Formula III is reacted at a temperature of from about 0° to about 60° C., with a 1.5:1 to 10:1 mixture of 1,2,4-triazole and an alkali metal salt of 1,2,4-triazole in the presence of a C$_1$–C$_4$ lower alkanol. The desired solid product can then be recovered employing conventional separatory techniques such as, filtration, decantation and the like. The product, if desired, can be further purified employing conventional techniques such as, solvent recrystallization. When this procedure is employed, only the asymmetrical triazole product is obtained.

The compounds wherein R is —C(O)R$^4$ can be prepared by reacting, at room temperature, an appropriate compound of Formula 1 wherein R is hydrogen with an appropriate acid anhydride of the formula O(C(O)R$^4$)$_2$ wherein R$^4$ is as defined hereinabove in a solvent, such as, for example, benzene, chloroform, methylene chloride, ethyl acetate or the like, and in the presence of a catalyst such as, for example, 4-dimethylaminopyridine. The product can be recovered employing conventional separatory procedures.

The salts and metal complexes of the compounds of Formula I can be prepared from the latter employing conventional procedures. The salts are obtained by mixing an approximate organic or inorganic acid with the compound of Formula I, if necessary in an inert solvent, distilling off the solvent and recrystallizing the residue as necessary. Alternately, water soluble salts such as phosphates and acetates may be prepared as aqueous solutions, for ease of formulation, by neutralization of the compound in an equimolar amount of the acid. Oil soluble acid derivatives such as the oleate may also be prepared by a similar means in an organic solvent such as xylene. The complexes, for example, can be prepared by reacting the uncomplexed compound with an appropriate metal salt in the presence of a suitable solvent.

The following Examples illustrate the present invention and the manner by which it can be practiced, but as such, should not be construed as limitations upon the overall scope of the same.

EXAMPLE I 1,1,1-Trichloro-3-(4-chlorophenyl)-3-hydroxy-4-(1,2,4-(1H)triazolyl)butane

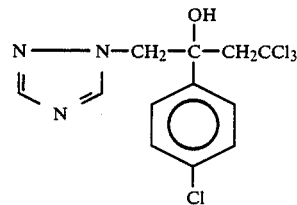

A solution was prepared by dissolving 24.0 g (1.043 moles) of sodium metal in 800 mL of methanol and adding 155.0 g (2.25 moles) of 1,2,4-triazole thereto. To this solution was added 140.0 g (0.490 mol) of 2-(4-chlorophenyl)-2-(2,2,2-trichloroethyl)oxirane dissolved in 200 mL of methanol.

The mixture was heated at 50° C. for 16 hours and allowed to stand at room temperature for 3 days. The reaction mixture was then cooled to 10° C. and 800 mL of water were added while the temperature was maintained at 10° C.

The resultant slurry was stirred at 10° C. for 30 minutes and filtered. The solid filter cake was washed twice with 250 mL of hexane. The solid was dried to give 149 g of a cream colored solid which melted at 130° C. This solid was then stirred in 1500 mL of chloroform and filtered through diatomaceous earth. Evaporation of the chloroform under reduced pressure and recrystallization of the residue from a substantially 1:2 benzene-hexane mixture gave the above named compound, as white crystals, in a yield of 129.6 g (74.5 percent of theoretical). The compound melted at 139° C.

| Elemental Analysis | % C | % H | % N |
|---|---|---|---|
| Calculated for C$_{12}$H$_{11}$Cl$_4$N$_3$O: | 40.59 | 3.12 | 11.84 |

| Elemental Analysis | % C | % H | % N |
| --- | --- | --- | --- |
| Found: | 40.73 | 3.09 | 11.88 |

By following the preparative procedures of Example I, the following compounds are prepared:

1,1,1-Trichloro-3-(3,5-dichlorophenyl)-3-hydroxy-4-(1,2,4-(1H)-triazolyl)butane, yield 81%, melting at 186° C.;

| Elemental Analysis | % C | % H | % N |
| --- | --- | --- | --- |
| Calc. for $C_{12}H_{10}Cl_5N_3O$: | 37.00 | 2.59 | 10.79 |
| Found: | 37.65 | 2.61 | 10.42 |

1,1,1-Trichloro-3-(4-fluorophenyl)-3-hydroxy-4-(1,2,4-(1H)-triazolyl)butane, yield 65%, melting at 153° C.;

| Elemental Analysis | % C | % H | % N |
| --- | --- | --- | --- |
| Calc. for $C_{12}H_{11}Cl_3FN_3O$: | 42.60 | 3.25 | 12.40 |
| Found: | 42.40 | 3.25 | 12.40 |

1,1,1-Trichloro-3-(2,4-difluorophenyl)-3-hydroxy-4-(1,2,4-(1H)-triazolyl)butane, melting at 127° C.;
1,1,1-Trichloro-3-(4-bromophenyl)-3-hydroxy-4-(1,2,4-(1H)-triazolyl)butane, melting at 136° C.;
1,1,1-Trichloro-3-phenyl-3-hydroxy-4-(1,2,4-(1H)-triazolyl)butane, melting at 111° C.;
1,1,1-Trichloro-3-(4-t-butylphenyl)-3-hydroxy-4-(1,2,4-(1H)-triazolyl)butane, melting at 108° C.;
1,1,1-Trichloro-3-((4-phenyl)phenyl)-3-hydroxy-4-(1,2,4-(1H)-triazolyl)butane, melting at 72° C.;
1,1,1-Trichloro-3-((4-trifluoromethyl)phenyl)-3-hydroxy-4-(1,2,4-(1H)-triazolyl)butane, melting at 105° C.;
1,1,1-Trifluoro-2,2-dichloro-4-(4-chlorophenyl)-4-hydroxy-5-(1,2,4-(1H)-triazolyl)pentane;
2,2-Dichloro-4-(4-chlorophenyl)-4-hydroxy-5-(1,2,4-(1H)-triazolyl)pentane; and
1,1,1-Trichloro-3-(4-methylphenyl)-3-hydroxy-4-(1,2,4-(1H)-triazolyl)butane, melting at 106° C.

EXAMPLE II 1,1,1-Trichloro-3-(3,5-dichlorophenyl)-3-hydroxy-4-(1,2,4-(1H)-triazolyl)butane

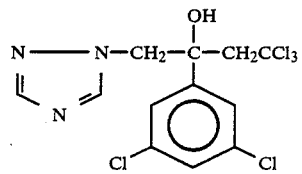

A solution of 32.0 g (0.10 mol) of 2-(3,5-dichlorophenyl)-2-(2,2,2-trichloroethyl)oxirane and 21.0 g (0.30 mol) of 1,2,4-triazole in 150 mL of glacial acetic acid was heated at 100° C. for six hours and cooled to room temperature. Most of the solvent was removed in vacuo, leaving the reaction product as an oil. The oil was dissolved in 800 mL of ethyl ether, washed thrice with 150 mL portions of water then with 150 mL of saturated brine. The organic portion was separated from the aqueous layer and dried over sodium sulfate. The solvent was removed in vacuo leaving 38.0 g of an oily residue. The residue was dissolved in 100 mL of ethyl acetate and to this solution was added 125 mL of hexane with a fine solid crystallizing out of solution.

The solid was recovered by filtration, washed with hexane and dried leaving 8.0 g of a crude solid product. The solid was taken up in 40 mL of isopropyl acetate, heated at reflux and cooled to room temperature. A white crystalline solid was collected by filtration and dried at 75° C. in vacuo leaving 6.2 g of a product which melted at 183°-184° C. Nuclear magnetic resonance spectrography showed the product to be a mixture of 75% 1,1,1-trichloro-3-(3,5-dichlorophenyl)-3-hydroxy-4-(1,2,4-(1H)-triazolyl)butane and 25% 1,1,1-trichloro-3-(3,5-dichlorophenyl)-3-hydroxy-4-(1,2,4-(4H)-triazolyl)butane. The two isomeric products were separated by column chromatography on silica gel.

Four and two-tenths grams of substantially pure 1,1,1-trichloro-3-(3,5-dichlorophenyl)-3-hydroxy-4-(1,2,4-(1H)-triazolyl)butane which melted at 187°-188° C. came off the column first using ethyl acetate as the eluent.

| Elemental Analysis | % C | % H | % N |
| --- | --- | --- | --- |
| Calc. for $C_{12}H_{10}Cl_5N_3O$: | 37.00 | 2.59 | 10.79 |
| Found: | 36.80 | 2.59 | 10.60 |

One gram of substantially pure 1,1,1-trichloro-3-(3,5-dichlorophenyl)-3-hydroxy-4-(1,2,4-(4H)-triazolyl)butane which melted at 221°-222° C., w/dec was then obtained using a 1:9 mixture of methanol and ethyl acetate as the eluent.

By following the preparative procedures of Example II, the following compounds are prepared:

1,1,1-Trichloro-3-(2,4-dichlorophenyl)-3-hydroxy-4-(1,2,4-(4H)-triazolyl)butane, as the hydrate; melting at 206°-206.5° C., w/dec.

| Elemental Analysis | % C | % H | % N |
| --- | --- | --- | --- |
| Calc. for $C_{12}H_{10}Cl_5N_3O \cdot H_2O$: | 35.36 | 2.97 | 10.31 |
| Found: | 35.10 | 3.01 | 10.22 |

1,1,1-Trichloro-3-(2,4-dichlorophenyl)-3-hydroxy-4-(1,2,4-(1H)-triazolyl)butane; melting at 139.5°-140.5° C.

| Elemental Analysis | % C | % H | % N |
| --- | --- | --- | --- |
| Calc. for $C_{12}H_{10}Cl_5N_3O$: | 37.00 | 2.59 | 10.79 |
| Found: | 37.50 | 2.54 | 10.74 |

EXAMPLE III

3-Acetoxy-1,1,1-trichloro-3-(4-chlorophenyl)-4-(1,2,4-(1H)-triazolyl)butane

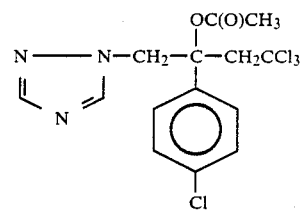

Five (5) g (0.0141 mol) of 4,4,4-trichloro-2-(4-chlorophenyl)-2-hydroxy-(1,2,4-(1H)-triazolyl)butane (prepared as in Example I) was slurried in 75 mls of benzene, 4.31 g (0.0422 mol) of acetic anhydride and 2.6 g (0.0211 mol) of 4-dimethylaminopyridine. This mixture was stirred at room temperature for 30 hours and then diluted with 75 mls of benzene. The mixture was washed thrice with 100 mL portions of water. Evaporation of the solvent under reduced pressure and purification of the residue by preparative high pressure liquid chromatography (HPLC) in a 1:1 mixture of ethyl acetate and hexane gave the desired product as a white solid in a yield of 2.2 g (39 percent of theoretical) melting at 112°–114° C.

| Elemental Analysis | % C | % H | % N |
|---|---|---|---|
| Calculated for $C_{12}H_{11}Cl_4N_3O$: | 42.34 | 3.30 | 10.58 |
| Found: | 42.50 | 3.30 | 10.50 |

By following the preparative procedure of Example III, the following compound is prepared:

3-Trifluoroacetoxy-1,1,1-trichloro-3-(4-chlorophenyl)-4-(1,2,4-(1H)-triazolyl)butane; melting at 127° C.

It has been found that the compounds of Formula I have a high degree of fungicidal activity. The compounds are especially effective in the kill and control of fungal organisms which attack plants. Representative fungal disease organisms controlled include:

*Alternaria brassicicola* (leaf spot of brassicas),
*Alternaria tenuis* (leaf spot),
*Botrytis cinerea* (grey mold),
*Cochliobolus sativus* (spot blotch),
*Colletotrichum coffeanum* (coffee berry disease),
*Colletotrichum lindemuthianum* (anthracnose of bean),
*Erysiphe graminis hordeii* (wheat powdery mildew),
*Erysiphe graminis tritici* (barley powdery mildew),
*Fusarium culmorum* (head blight),
*Fusarium oxysporum fsp phaseolicola*,
*Gerlachia nivalis* (snow mold),
*Phytophthora citricola*,
*Phytophthora parasitica* (black shank),
*Plasmopara viticola* (grape downy mildew),
*Podosphaera leucotricha* (apple powdery mildew),
*Pseudocercosporella herpotrichoides* (cereal eye spot),
*Puccinia recondita* (brown rust),
*Pyrenophpora teres* (net blotch of barley),
*Pyricularia oryzae* (rice blast),
*Pythium ultimum* (damping off),
*Rhizoctonia cerealis* (sharp eye spot of wheat),
*Rhizoctonia solani* (root rot),
*Rhychosporium secalis* (leaf scald),
*Septoria ssp* (cereal leaf spot),
*Sclerotium rolfsii* (white rot),
*Sclerotinia sclerotiorum*,
*Verticillium albo-atrum* (wilt of tomatoes) and
*Venturia inaequalis* (apple scab).

Compositions containing the present compounds can be applied to the roots, seeds or foliage of the plants and will kill or control the growth of various fungi without damaging the commercial value of said plants. Many of these compositions are unique because of their systemic action and because of the very low levels of chemical required to control the fungal organism.

These chemicals may be prepared as dusts, wettable powders, flowable concentrates, suspension concentrates or emulsifiable concentrates.

The present invention includes within its scope a method for the control of fungus diseases attacking plants or plant parts which method comprises applying to the plants, the plant parts or to the organisms or to their habitats compositions containing one or more of the active compounds.

Another advantage of the present invention is that a single application of the compositions can provide a residual control of the fungal diseases over an extended period. Also, the compounds can be effective in eliminating established fungal infestations. Furthermore, many compounds have been found to be translocated in plants and, thus, can provide a systemic protection.

The method of the present invention comprises contacting plants, especially cereal grain plants, with a fungicidal amount of a composition containing one or more of the active compounds. The present invention also embraces the employment of a liquid, powder, dust or granular composition containing one or more of the active compounds in intimate admixture with inert, nonphytotoxic materials, known in the art as agricultural adjuvants and/or carriers, in solid or liquid form.

Thus, for example, the active compound(s) can be admixed with one or more additives including organic solvents, petroleum distillates, water or other liquid carriers, surface active dispersing agents, and finely divided inert solids. In such compositions, the active ingredients are present in a concentration from about 2.0 percent to about 95.0 percent by weight, preferably 5.0 percent to about 95.0 percent by weight and most advantageously 5.0 percent to about 75.0 percent by weight.

The compound can be employed in the form of diluted flowable/suspension concentrate compositions or a wettable powder composition containing 2 to 10,000 ppm of one or more of the compounds, preferably 10 to 600 ppm are employed. When the carrier contains a surface active agent, from about 0.1 to about 20.0 percent by weight of the active ingredient is advantageously employed. Depending upon the concentration in the composition, such augmented compositions are adapted to be employed for the control of the undesirable fungi or employed as concentrates and subsequently diluted with additional inert carrier, e.g., water, to produce the ultimate treating compositions.

In general, good results can be obtained with liquid compositions containing from about 0.0001 to about 2.0 percent by weight of the toxicant in the final diluted form. With dusts, good results can usually be obtained with compositions containing from about 0.1 to about 2.0 percent or more by weight of toxicant. Where the compositions are to be applied to foliage of plants to control the fungal organism, it is preferred that the toxicant be present in an amount not to exceed about 0.8 percent in liquid compositions and about 1.0 percent in dusts.

In terms of hectare application, good controls can be obtained when the active ingredients are applied to growing plants at a dosage of from about 0.004 to about 4.0 kg/hectare.

When employed as fungicides for the treatment of seeds or non-living substrates, from about 0.05 to about 1.0 gram of the active compound per kilogram of substrate is an effective dose.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. Dust compositions are advantageously employed when treating seeds.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and/or oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water.

Emulsifiers which can be advantageously employed herein can be readily determined by those skilled in the art and include various nonionic and anionic emulsifiers, or a blend of two or more of said emulsifiers.

Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with a polyol or polyoxyalkylene.

Anionic emulsifiers include the oil-soluble salts (e.g., calcium) of alkylaryl sulphonic acids, oil soluble salts of sulphated polyglycol ethers and appropriate salts of phosphated polyglycol ether.

The preferred emulsifiers will depend upon the nature of the emulsifiable concentrate and the desired use of said concentrate; the selection of the specific emulsifier follows conventional formulation practices and is well known to those skilled in the art. For example, an emulsifiable concentrate of a compound of Formula I containing 200 g/L of the compound in xylene may require a blend of an ethoxylated nonyl phenol and calcium dodecyl benzene sulfonate to function effectively whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions; mineral oils; substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol and ketones such as cyclohexanone, isophorone and dihydroisophorone. Mixtures of two or more organic liquids are also often suitably employed in the preparation of the emulsifiable concentrate. The preferred organic liquids are ketones, especially isophorone-xylene mixtures, xylene, and propyl benzene fractions, with xylene being most preferred.

The surface active dispersing agents are usually employed in liquid compositions and in the amount of from 0.1 to 20.0 percent by weight of the combined weight of the dispersing agent and active compound.

The active compositions can also contain other compatible additaments, for example, plant growth regulators and other biologically active compounds used in agriculture.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulfosuccinic acids, ethoxylated organosilicones, ethoxylated fatty amines and blends of surfactant with mineral or vegetable oils. Mixtures of the above adjuvant systems can be employed to optimize the biological performance of the compounds of the present invention.

In such embodiments, the compounds of the present invention or compositions containing the same, can be advantageously employed in combination with one or more additional pesticidal compounds. Such additional pesticidal compounds may be insecticides, nematicides, miticides, arthropodicides, or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The exact amount of the active material to be applied is dependent not only on the specific active material being applied, but also on the particular action desired, the fungal species to be controlled and the stage of growth thereof as well as the part of the plant to be contacted with the toxic active ingredient. Thus, all of the active ingredients of the present invention and compositions containing the same may not be equally effective at similar concentrations or against the same fungal species.

The following active compounds set forth below in Table II were evaluated for fungicidal activity:

TABLE II

| Compound No. | Active Compound |
|---|---|
| 1 | 1,1,1-Trichloro-3-(3,5-dichlorophenyl)-3-hydroxy-4-(1,2,4-(1H)-triazolyl)butane |
| 2 | 1,1,1-Trichloro-3-(3,5-dichlorophenyl)-3-hydroxy-4-(1,2,4-(4H)-triazolyl)butane |
| 3 | 1,1,1-Trichloro-3-(2,4-dichlorophenyl)-3-hydroxy-4-(1,2,4-(4H)-triazolyl)butane |
| 4 | 1,1,1-Trichloro-3-(2,4-dichlorophenyl)-3- |

TABLE II-continued

| Compound No. | Active Compound |
|---|---|
|  | hydroxy-4-(1,2,4-(1H)-triazolyl)butane |
| 5 | 1,1,1-Trichloro-3-(4-chlorophenyl)-3-hydroxy-4-(1,2,4-(1H)-triazolyl)butane |
| 6 | 1,1,1-Trichloro-3-(4-fluorophenyl)-3-hydroxy-4-(1,2,4-(1H)-triazolyl)butane |
| 7 | 3-Acetoxy-1,1,1-trichloro-3-(4-chlorophenyl)-4-(1,2,4-(1H)-triazolyl)butane |
| 8 | 1,1,1-Trichloro-3-(2,4-difluorophenyl)-3-hydroxy-4-(1,2,4-(1H)-triazolyl)butane |
| 9 | 1,1,1-Trichloro-3-(4-bromophenyl)-3-hydroxy-4-(1,2,4-(1H)-triazolyl)butane |
| 10 | 1,1,1-Trichloro-3-phenyl-3-hydroxy-4-(1,2,4-(1H)-triazolyl)butane |
| 11 | 1,1,1-Trichloro-3-(4-t-butylphenyl)-3-hydroxy-4-(1,2,4-(1H)-triazolyl)butane |
| 12 | 1,1,1-Trichloro-3-((4-phenyl)phenyl)-3-hydroxy-4-(1,2,4-(1H)-triazolyl)butane |
| 13 | 1,1,1-Trichloro-3-((4-trifluoromethyl)phenyl)-3-hydroxy-4-(1,2,4-(1H)-triazolyl)butane |
| 14 | 1,1,1-Trifluoro-2,2-dichloro-4-(4-chlorophenyl)-4-hydroxy-5-(1,2,4-(1H)-triazolyl)pentane |
| 15 | 3-Trifluoroacetoxy-1,1,1-trichloro-3-(4-chlorophenyl)-4-(1,2,4-(1H)-triazolyl)butane |
| 16 | 2,2-Dichloro-4-(4-chlorophenyl)-4-hydroxy-5-(1,2,4-(1H)-triazolyl)pentane |
| 17 | 1,1,1-Trichloro-3-(4-methylphenyl)-3-hydroxy-4-(1,2,4-(1H)-triazolyl)butane |

Representative formulations/compositions of the present invention include the following:

TABLE III

Emulsifiable Concentrates

| Ingredient | weight % of total composition |
|---|---|
| Compound of Example 5 | 10.0 |
| AGRILAN BM ® | 5.0 |
| (a proprietary anionic/nonionic surfactant blend of Lankro Chemicals) | |
| ATLOX 48518 ® | 5.0 |
| (a proprietary anionic/nonionic surfactant blend of ICI Specialty Chemicals) | |
| Dihydroisophorone | 80.0 |

TABLE IV

Wettable Powders

| Ingredient | weight % of total composition |
|---|---|
| Compound of Example 5 | 10.0 |
| AEROSOL OT-B ® | 1.0 |
| (sodium dioctyl sulfosuccinate) | |
| DYAPOL PT ® | 5.0 |
| (a proprietary dispersing agent of Yorkshire Chemicals) | |
| Barden Clay | 84.0 |

TABLE V

Flowable Concentrates

| Ingredient | weight % of total composition |
|---|---|
| Compound of Example 5 | 10.0 |
| AGRILAN F502 ® | 2.0 |
| (a proprietary material of Lankro Chemicals) | |
| DARVAN NO. 1 ® | 2.0 |
| (a proprietary material of W. R. Grace & Co.) | |
| FOAMASTER UDB ® | 0.1 |
| (a proprietary material of Lankro Chemicals) | |
| DOWICIDE A ® | 0.05 |
| (a proprietary material of | |

TABLE V-continued

Flowable Concentrates

| Ingredient | weight % of total composition |
|---|---|
| The Dow Chemical Co.) | |
| KELZAN ® | 0.1 |
| (a proprietary material of Kelco Co.) | |
| Propylene Glycol | 5.0 |
| Water | 80.75 |

TABLE VI

Dusts

| Ingredient | weight % of total composition |
|---|---|
| Compound of Example 5 | 1.0 |
| NEOSYL ® | 5.0 |
| (a proprietary material of J. Crosfields Co.) | |
| Barden Clay | 94.0 |

The method for evaluating in vivo fungicidal activity consists of applying the test compound, in diluted form, to a host plant. The plants are inoculated with the fungus (in spore form) and stored in a greenhouse or other controlled environment until untreated plants, used as controls, become infested with the fungus. The treated plants are then visually inspected and assigned a rating based on the percentage of total leaf area that has not become infested.

Formulations containing the test compounds are prepared from concentrates in acetone. The compound (0.04 g) was dissolved in 10 mL of acetone and 90 mL of water and 2 drops of a wetting agent were added to form a 400 ppm solution of the active compound for application to leaves or roots.

Barley Powdery Mildew

Procedure A: Soil Drench Test

Barley seeds cv Golden Promise were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with conidia of *Erysiphe graminis hordeii* by brushing the foliage with heavily sporulating plants. The plants were assessed for disease levels 10 days later by comparing the sporulation on plants treated with the experimental chemical to untreated but inoculated control plants.

Procedure B: Foliar Application

Barley was grown as for the above soil drench test. The foliage of the plants was sprayed with a 400 ppm solution of the test chemical. The treated plants were held under greenhouse conditions for 24 hours and then inoculated with conidia of *Erysiphe graminis hordeii* by brushing the foliage with heavily sporulating plants. The plants were assessed for disease levels 10 days later by comparing the sporulation on plants treated with the experimental chemical to untreated but inoculated control plants.

Barley Spot Blotch

Procedure C: Soil Drench Test

Barley seeds cv Gerbel were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with conidia of *Cochliobolus sativus* by brushing the foliage with heavily sporulating plants. The plants were assessed for disease levels 7 days later by comparing the sporulation on plants treated with the experimental chemical to untreated but inoculated control plants.

Procedure D: Foliar Application

Barley was grown as for the above soil drench test. The foliage of the plants was sprayed with a 400 ppm solution of the test chemical. The treated plants were held under greenhouse conditions for 24 hours and then inoculated with conidia of *Cochliobolus sativus* by brushing the foliage with heavily sporulating plants. The plants were assessed for disease levels 7 days later by comparing the sporulation on plants treated with the experimental chemical to untreated but inoculated control plants.

Brown Rust

Procedure E: Soil Drench Test

Wheat seeds cv Armada were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with a dense talc/spore suspension of *Puccinia recondita.* The plants were placed into a chamber with 100 percent relative humidity for 24 hours and then removed and held in a greenhouse for 7 days and assessed when symptoms of the disease appeared on untreated but inoculated control plants.

Procedure F: Foliar Application

Wheat was grown as for the above soil drench test. The foliage of the plants was sprayed with a 400 ppm solution of the test chemical. The treated plants were held under greenhouse conditions for 24 hours and then inoculated with a dense talc/spore suspension of *Puccinia recondita.* The plants were placed into a chamber with 100 percent relative humidity for 24 hours and then removed and held in a greenhouse for 7 days and assessed when symptoms of the disease appeared on the untreated but inoculated control plants.

Rice Blast

Procedure G: Soil Drench Test

Barley seeds cv Golden Promise were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with $1\times10^6$ conidia per mL of *Pyricularia oryzae* (rice blast) by spraying the spores onto the leaves. The plants were placed into a chamber with 100 percent relative humidity for 48 hours and then removed and held in a greenhouse for 5 to 7 days and assessed when symptoms of the disease appeared on untreated but inoculated control plants.

Procedure H: Foliar Application

Barley was grown as for the above soil drench test. The foliage of the plants was sprayed with a 400 ppm solution of the test chemical. The treated plants were held under greenhouse conditions for 24 hours and then inoculated with $1\times10^6$ conidia per mL of *Pyricularia oryzae* (rice blast) by spraying the spores onto the leaves. The plants were placed into a chamber with 100 percent relative humidity for 48 hours and then removed and held in a greenhouse for 5 to 7 days and assessed when symptoms of the disease appeared on the untreated but inoculated control plants.

The results of test of procedures A, B, C, D, E, F, G and H are set forth hereinafter in Table VII.

TABLE VII

| | Percent control at 400 ppm of indicated organism | | | | | | | |
|---|---|---|---|---|---|---|---|---|
| Comp | *Erysiphe graminis hordeii* | | *Puccinia recondita*** | | *Cochliobolus sativus* | | *Pyricularia oryzae* | |
| No.* | soil | foliar | soil | foliar | soil | foliar | soil | foliar |
| 1 | 100 | 50 | 0 | 0 | NT | NT | <80 | <80 |
| 2 | 0 | 0 | 0 | 50 | NT | NT | <80 | <80 |
| 3 | 0 | 25 | 0 | 80 | NT | NT | 70 | 100 |
| 4 | 100 | 100 | 0 | 100 | 10 | 95 | 90 | 99 |
| 5 | 100 | 100 | 100 | 100 | 10 | 75 | <80 | <80 |
| 6 | 100 | 100 | 100 | 100 | 90 | 95 | <80 | <80 |
| 7 | 100 | NT | 50 | 100 | 0 | 0 | <80 | <80 |
| 8 | NT | 100 | NT | NT | NT | NT | NT | 39 |
| 9 | NT | 100 | NT | NT | NT | NT | NT | 17 |
| 10 | NT | 100 | NT | NT | NT | NT | NT | 50 |
| 11 | NT | 63 | NT | NT | NT | NT | NT | 44 |
| 12 | NT | 93 | NT | NT | NT | NT | NT | 61 |
| 13 | NT | 100 | NT | NT | NT | NT | NT | 56 |
| 14 | NT | 100 | NT | NT | NT | NT | NT | 22 |
| 15 | NT | 100 | NT | NT | NT | NT | NT | 44 |
| 16 | NT | 100 | NT | NT | NT | NT | NT | 73 |

TABLE VII-continued

| | Percent control at 400 ppm of indicated organism | | | | | | | |
|---|---|---|---|---|---|---|---|---|
| | Erysiphe graminis hordeii | | Puccinia recondita** | | Cochliobolus sativus | | Pyricularia oryzae | |
| Comp No.* | soil | foliar | soil | foliar | soil | foliar | soil | foliar |
| 17 | NT | 87 | NT | NT | NT | NT | NT | 44 |

*Compound Nos. correspond to those in Table II.
**Test conducted at a treating rate of 100 ppm.

In other in vivo tests, compound numbers 8, 9 and 11–17 were found at 400 ppm to give varying amounts of kill and control of *Plasmopara viticola* when plants were sprayed with the test compound prior to inoculation with spores of the fungal organism.

The specific procedure employed in in vitro test to evaluate the active compounds against particular fungal organisms is as follows:

In vitro test

Procedure I

Test chemicals were added to liquid potato dextrose agar in plastic petri dishes at a final concentration of 40 ppm and then the agar allowed to cool and set to a solid. Discs of actively growing fungi of the following plants pathogenic species: *Alternaria brassisicola, Botrytis cinera, Colletotrichum lindemuthianum, Fusarium oxysporum* fsp. *phaseolicola, Pyrenophora teres, Pythium ultimum, Sclerotium rolfsii,* and *Verticillium albo-atrum* were placed onto the chemical incorporated agar. Radial growth of the fungi was measured after 3–5 days when growth of the fungi on the untreated agar had reached a maximum. The results of said test are set forth hereinafter in Table VIII.

TABLE VIII

| Comp. No. | AB | FOP | PT | VA | BC | CL | SR | PU |
|---|---|---|---|---|---|---|---|---|
| 8 | 100 | 95 | 96 | 100 | 35 | 79 | 100 | 25 |
| 9 | 58 | 68 | 78 | 80 | 0 | 53 | 100 | 33 |
| 10 | 72 | 94 | 80 | 83 | 0 | 32 | 77 | 25 |
| 11 | 36 | 65 | 65 | 33 | 0 | 26 | 77 | 46 |
| 12 | 46 | 67 | 82 | 27 | 0 | 37 | 100 | 13 |
| 13 | 40 | 61 | 63 | 43 | 0 | 37 | 100 | 25 |
| 14 | 66 | 70 | 80 | 93 | 0 | 47 | 100 | 36 |
| 15 | 62 | 80 | 75 | 97 | 0 | 53 | 100 | 30 |
| 16 | 86 | 83 | 84 | 100 | 89 | 79 | 100 | 32 |
| 17 | 56 | 78 | 75 | 97 | 0 | 63 | 100 | 34 |

AB = *Alternaria brassiciola*
FOP = *Fusarium oxysporum fsp phaseolicola*
PT = *Pyrenophpra teres*
VA = *Verticillium albo-atrum*
BC = *Botrytis cinerea*
CL = *Colletotrichum lindemuthianum*
SR = *Sclerotium rolfsii*
PU = *Pythium ultimum*

When one or more of the compounds of the present invention were applied at dosage levels of between 2.0 and 400.0 ppm, they had the ability to kill, inhibit or otherwise control one or more fungal diseases of plants.

Starting Materials

The oxirane compounds employed herein are for the most part well known compounds and those that are not specifically known can be prepared employing procedures analogous to those employed to prepare specifically known oxirane compounds.

Those compounds corresponding to Formula IV

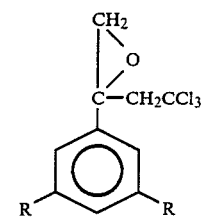
(IV)

wherein R is —Br, —Cl or —CH$_3$ are taught in U.S. Pat. No. 4,211,549.

Those compounds corresponding to Formula V

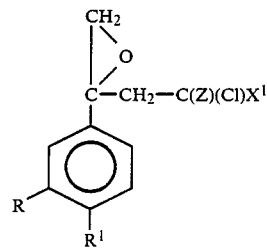
(V)

wherein X$^1$ represents halo; Z represents —H, halo, —CN or alkyl; R and R$^1$ each independently represent —H, —CN, nitro, alkoxy, —CF$_3$, benzyloxy or alkyl, with the proviso that when R$^1$ is —H, R is other than —H are taught in U.S. Pat. No. 4,018,801.

The compounds corresponding to Formula VI

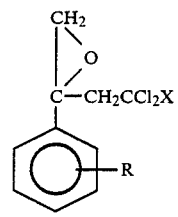
(VI)

wherein X represents —H, —Cl or —CH$_3$; R represents, in the 3, 4 or 5 ring position, —CF$_3$, alkyl, alkoxy, Br, Cl, F or nitro can be prepared employing the same procedure as taught in U.S. Pat. No. 4,211,549 using the appropriate starting materials.

Those compounds corresponding to Formula VII

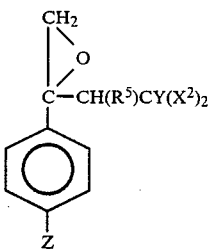

(VII)

wherein Z represents —H or —Cl and $R^5$ represents —H or straight chain alkyl; each $X^2$ is halo; and Y can be $X^2$ and if at least one of $X^2$ is bromo, Y can also be —H, are taught in Canadian Patent 527,462.

The compounds corresponding to the formula

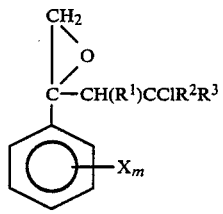

(III)

wherein $R^1$, $R^2$, $R^3$, X and m are as hereinabove set forth can be prepared employing the same procedure as taught in Canadian Patent 527,462 using the appropriate starting materials.

What is claimed is:

1. A substituted triazole compound corresponding to the formulae

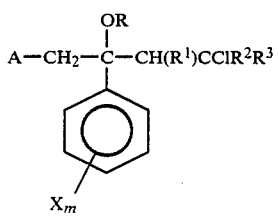

(Formula I)

wherein

A represents

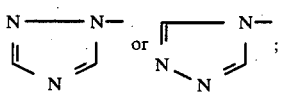

R represents —H, or —C(O)$R^4$;

$R^1$ and $R^2$ each independently represent —H, halo, $C_1$–$C_4$ straight chain alkyl;

$R^3$ represents —H, halo, $C_1$–$C_4$ alkyl, $C_1$–$C_4$-haloalkyl, —CN, or —C(O)N$R^5R^6$;

$R^4$ represents $C_1$–$C_4$ alkyl, $C_1$–$C_2$ haloalkyl, phenyl or phenyl substituted by $C_1$–$C_6$ alkyl or halo;

$R^5$ and $R^6$ each independently represent —H, —CN, $C_1$–$C_4$ alkyl, $C_3$–$C_8$ cycloalkyl, phenyl or phenylalkyl having 1 to 6 carbon atoms in the alkyl moiety;

each X independently represents —H, halo, —CN, $C_1$–$C_4$ alkyl, $C_1$–$C_4$ haloalkyl, $C_1$–$C_4$ alkoxy, $C_1$–$C_4$ alkoxy, nitro, phenyl or benzyloxy;

m represents 1 to 3; and the acid addition salts and metal complexes thereof, with the proviso that when m is greater than 1, X is only in the 2, 3, 4 or 5 ring positions.

2. A compound as defined in claim 1 wherein R represents —H or —C(O)$R^4$, $R^1$ is —H, $R^2$ is halo, $R^3$ is halo or haloalkyl, $R^4$ is alkyl or haloalkyl and X is —H, halo, alkyl, haloalkyl or phenyl.

3. A compound as defined in claim 2 wherein m is 0, 1 or 2.

4. A compound as defined in claim 3 wherein R represents —H or —C(O)$R^4$, $R^1$ is —H, $R^2$ is chloro, $R^3$ is chloro or trifluoromethyl, $R^4$ is methyl or trifluoromethyl and X is —H, halo, methyl, trifluoromethyl or phenyl.

5. A compound as defined in claim 4 wherein R is —H.

6. The compound as defined in claim 5 which is 1,1,1-trichloro-3-(3,5-dichlorophenyl)-3-hydroxy-4-(1,2,4-(1H)-triazolyl)butane.

7. The compound as defined in claim 5 which is 1,1,1-trichloro-3-(3,5-dichlorophenyl)-3-hydroxy-4-(1,2,4-(4H)-triazolyl)butane.

8. The compound as defined in claim 5 which is 1,1,1-trichloro-3-(2,4-dichlorophenyl)-3-hydroxy-4-(1,2,4-(4H)-triazolyl)butane.

9. The compound as defined in claim 5 which is 1,1,1-trichloro-3-(2,4-dichlorophenyl)-3-hydroxy-4-(1,2,4-(1H)-triazolyl)butane.

10. The compound as defined in claim 5 which is 1,1,1-trichloro-3-(4-chlorophenyl)-3-hydroxy-4-(1,2,4-(1H)-triazolyl)butane.

11. The compound as defined in claim 5 which is 1,1,1-trichloro-3-(4-fluorophenyl)-3-hydroxy-4-(1,2,4-(1H)-triazolyl)butane.

12. The compound as defined in claim 5 which is 1,1,1-trichloro-3-(2,4-difluorophenyl)-3-hydroxy-4-(1,2,4-(1H)-triazolyl)butane.

13. The compound as defined in claim 5 which is 1,1,1-trichloro-3-(4-bromophenyl)-3-hydroxy-4-(1,2,4-(1H)-triazolyl)butane.

14. The compound as defined in claim 5 which is 1,1,1-trichloro-3-phenyl-3-hydroxy-4-(1,2,4-(1H)-triazolyl)butane.

15. The compound as defined in claim 5 which is 1,1,1-trichloro-3-(4-t-butylphenyl)-3-hydroxy-4-(1,2,4-(1H)-triazolyl)butane.

16. The compound as defined in claim 5 which is 1,1,1-trichloro-3-((4-phenyl)phenyl)-3-hydroxy-4-(1,2,4-(1H)-triazolyl)butane.

17. The compound as defined in claim 5 which is 1,1,1-trichloro-3-((4-trifluoromethyl)phenyl)-3-hydroxy-4-(1,2,4-(1H)-triazolyl)butane.

18. The compound as defined in claim 5 which is 1,1,1-trifluoro-2,2-dichloro-4-(4-chlorophenyl)-4-hydroxy-5-(1,2,4-(1H)-triazolyl)pentane.

19. The compound as defined in claim 5 which is 2,2-dichloro-4-(4-chlorophenyl)-4-hydroxy-5-(1,2,4-(1H)-triazolyl)pentane.

20. The compound as defined in claim 5 which is 1,1,1-trichloro-3-(4-methylphenyl)-3-hydroxy-4-(1,2,4-(1H)-triazolyl)butane.

21. A compound as defined in claim 4 wherein R is —C(O)$R^4$.

22. The compound as defined in claim 21 which is 3-acetoxy-1,1,1-trichloro-3-(4-chlorophenyl)-4-(1,2,4-(1H)-triazolyl)butane.

23. The compound as defined in claim 21 which is 3-trifluoroacetoxy-1,1,1-trichloro-3-(4-chlorophenyl)-4-(1,2,4-(1H)-triazolyl)butane.

24. A fungicidal composition which comprises an inert carrier in intimate admixture with a fungicidally effective amount of an active ingredient which is a substituted triazole compound corresponding to the formulae

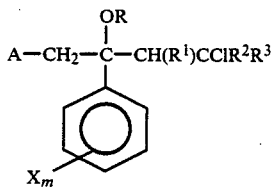 (Formula I)

wherein
A represents

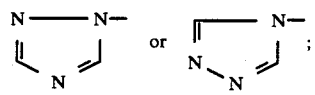

R represents —H, or —C(O)R$^4$;
R$^1$ and R$^2$ each independently represent —H, halo, C$_1$-C$_4$ straight chain alkyl;
R$^3$ represents —H, halo, C$_1$-C$_4$ alkyl, C$_1$-C$_4$-haloalkyl, —CN, or —C(O)NR$^5$R$^6$;
R$^4$ represents C$_1$-C$_4$ alkyl, C$_1$-C$_2$ haloalkyl, phenyl or phenyl substituted by C$_1$-C$_6$ alkyl or halo;
R$^5$ and R$^6$ each independently represent —H, —CN, C$_1$-C$_4$ alkyl, C$_3$-C$_8$ cycloalkyl, phenyl or phenylalkyl having 1 to 6 carbon atoms in the alkyl moiety;
each X independently represents —H, halo, —CN, C$_1$-C$_4$ alkyl, C$_1$-C$_4$ haloalkyl, C$_1$-C$_4$ alkoxy, C$_1$-C$_4$ alkoxy, nitro, phenyl or benzyloxy;
m represents 1 to 3; and
the acid addition salts and metal complexes thereof, with the proviso that when m is greater than 1, X is only in the 2, 3, 4 or 5 ring positions.

25. A composition as defined in claim 24 wherein R represents —H or —C(O)R$^4$, R$^1$ is —H, R$^2$ is halo, R$^3$ is halo or haloalkyl, R$^4$ is alkyl or haloalkyl and X is —H, halo, alkyl, haloalkyl or phenyl.

26. A composition as defined in claim 25 wherein m is 0, 1 or 2.

27. A composition as defined in claim 26 wherein R represents —H or —C(O)R$^4$, R$^1$ is —H, R$^2$ is chloro, R$^3$ is chloro or trifluoromethyl, R$^4$ is methyl or trifluoromethyl and X is —H, halo, methyl, trifluoromethyl or phenyl.

28. A composition as defined in claim 27 wherein wherein R is —H.

29. The composition as defined in claim 28 wherein the active ingredient is 1,1,1-trichloro-3-(3,5-dichlorophenyl)-3-hydroxy-4-(1,2,4-(1H)-triazolyl)butane.

30. The composition as defined in claim 28 wherein the active ingredient is 1,1,1-trichloro-3-(3,5-dichlorophenyl)-3-hydroxy-4-(1,2,4-(4H)-triazolyl)butane.

31. The composition as defined in claim 28 wherein the active ingredient is 1,1,1-trichloro-3-(2,4-dichlorophenyl)-3-hydroxy-4-(1,2,4-(4H)-triazolyl)butane.

32. The composition as defined in claim 28 wherein the active ingredient is 1,1,1-trichloro-3-(2,4-dichlorophenyl)-3-hydroxy-4-(1,2,4-(1H)-triazolyl)butane.

33. The composition as defined in claim 28 wherein the active ingredient is 1,1,1-trichloro-3-(4-chlorophenyl)-3-hydroxy-4-(1,2,4-(1H)-triazolyl)butane.

34. The composition as defined in claim 28 wherein the active ingredient is 1,1,1-trichloro-3-(4-fluorophenyl)-3-hydroxy-4-(1,2,4-(1H)-triazolyl)butane.

35. The composition as defined in claim 28 wherein the active ingredient is 1,1,1-trichloro-3-(2,4-difluorophenyl)-3-hydroxy-4-(1,2,4-(1H)-triazolyl)butane.

36. The composition as defined in claim 28 wherein the active ingredient is 1,1,1-trichloro-3-(4-bromophenyl)-3-hydroxy-4-(1,2,4-(1H)-triazolyl)butane.

37. The composition as defined in claim 28 wherein the active ingredient is 1,1,1-trichloro-3-phenyl-3-hydroxy-4-(1,2,4-(1H)-triazolyl)butane.

38. The composition as defined in claim 28 wherein the active ingredient is 1,1,1-trichloro-3-(4-t-butylphenyl)-3-hydroxy-4-(1,2,4-(1H)-triazolyl)butane.

39. The composition as defined in claim 28 wherein the active ingredient is 1,1,1-trichloro-3-((4-phenyl)-phenyl)-3-hydroxy-4-(1,2,4-(1H)-triazolyl)butane.

40. The composition as defined in claim 28 wherein the active ingredient is 1,1,1-trichloro-3-((4-fluoromethyl)phenyl)-3-hydroxy-4-(1,2,4-(1H)-triazolyl)butane.

41. The composition as defined in claim 28 wherein the active ingredient is 1,1,1-trifluoro-2,2-dichloro-4-(4-chlorophenyl)-4-hydroxy-5-(1,2,4-(1H)-triazolyl)pentane.

42. The composition as defined in claim 28 wherein the active ingredient is 2,2-dichloro-4-(4-chlorophenyl)-4-hydroxy-5-(1,2,4-(1H)-triazolyl)pentane.

43. The composition as defined in claim 28 wherein the active ingredient is 1,1,1-trichloro-3-(4-methylphenyl)-3-hydroxy-4-(1,2,4-(1H)-triazolyl)butane.

44. A composition as defined in claim 27 wherein R is —C(O)R$^4$.

45. The composition as defined in claim 44 wherein the active ingredient is 3-acetoxy-1,1,1-trichloro-3-(4-chlorophenyl)-4-(1,2,4-(1H)-triazolyl)butane.

46. A composition as defined in claim 44 wherein the active ingredient is 3-trifluoroacetoxy-1,1,1-trichloro-3-(4-chlorophenyl)-4-(1,2,4-(1H)-triazolyl)butane.

47. A method for the kill or control of fungal organisms which comprises contacting said organisms or their habitat with a fungicidal composition which comprises an inert carrier in intimate admixture with a fungicidally effective amount of an active ingredient which is a substituted triazole compound corresponding to the formulae

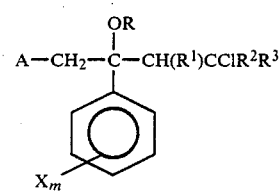 (Formula I)

wherein
A represents

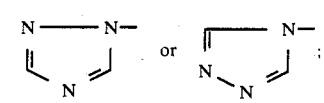

R represents —H, or —C(O)R$^4$;

$R^1$ and $R^2$ each independently represent —H, halo, $C_1$–$C_4$ straight chain alkyl;

$R^3$ represents —H, halo, $C_1$–$C_4$ alkyl, $C_1$–$C_4$-haloalkyl, —CN, or —C(O)NR$^5$R$^6$;

$R^4$ represents $C_1$–$C_4$ alkyl, $C_1$–$C_2$ haloalkyl, phenyl or phenyl substituted by $C_1$–$C_6$ alkyl or halo;

$R^5$ and $R^6$ each independently represent —H, —CN, $C_1$–$C_4$ alkyl, $C_3$–$C_8$ cycloalkyl phenyl or phenylalkyl having 1 to 6 carbon atoms in the alkyl moiety;

each X independently represents —H, halo, CN, $C_1$–$C_4$ alkyl, $C_1$–$C_4$ haloalkyl, $C_1$–$C_4$ alkoxy, $C_1$–$C_4$ alkoxy, nitro, phenyl or benzyloxy;

m represents 1 to 3; and the acid addition salts and metal complexes thereof, with the proviso that when m is greater than 1, X is only in the 2, 3, 4 or 5 ring positions.

48. A method as defined in claim 46 wherein R represents —H or —C(O)R$^4$, $R^1$ is —H, $R^2$ is halo, $R^3$ is halo or haloalkyl, $R^4$ is alkyl or haloalkyl and X is —H, halo, alkyl, haloalkyl or phenyl.

49. A method as defined in claim 47 wherein m is 0, 1 or 2.

50. A method as defined in claim 48 wherein R represents —H or —C(O)R$^4$, $R^1$ is —H, $R^2$ is chloro, $R^3$ is chloro or trifluoromethyl, $R^4$ is methyl or trifluoromethyl and X is —H, halo, methyl, trifluoromethyl or phenyl.

51. A method as defined in claim 49 wherein wherein R is —H.

52. The method as defined in claim 50 wherein the active ingredient is 1,1,1-trichloro-3-(3,5-dichlorophenyl)-3-hydroxy-4-(1,2,4-(1H)-triazolyl)butane.

53. The method as defined in claim 50 wherein the active ingredient is 1,1,1-trichloro-3-(3,5-dichlorophenyl)-3-hydroxy-4-(1,2,4-(4H)-triazolyl)butane.

54. The method as defined in claim 50 wherein the active ingredient is 1,1,1-trichloro-3-(2,4-dichlorophenyl)-3-hydroxy-4-(1,2,4-(4H)-triazolyl)butane.

55. The method as defined in claim 50 wherein the active ingredient is 1,1,1-trichloro-3-(2,4-dichlorophenyl)-3-hydroxy-4-(1,2,4-(1H)-triazolyl)butane.

56. The method as defined in claim 50 wherein the active ingredient is 1,1,1-trichloro-3-(4-chlorophenyl)-3-hydroxy-4-(1,2,4-(1H)-triazolyl)butane.

57. The method as defined in claim 50 wherein the active ingredient is 1,1,1-trichloro-3-(4-fluorophenyl)-3-hydroxy-4-(1,2,4-(1H)-triazolyl)butane.

58. The method as defined in claim 50 wherein the active ingredient is 1,1,1-trichloro-3-(2,4-difluorophenyl)-3-hydroxy-4-(1,2,4-(1H)-triazolyl)butane.

59. The method as defined in claim 50 wherein the active ingredient is 1,1,1-trichloro-3-(4-bromophenyl)-3-hydroxy-4-(1,2,4-(1H)-triazolyl)butane.

60. The method as defined in claim 50 wherein the active ingredient is 1,1,1-trichloro-3-phenyl-3-hydroxy-4-(1,2,4-(1H)-triazolyl)butane.

61. The method as defined in claim 50 wherein the active ingredient is 1,1,1-trichloro-3-(4-t-butylphenyl)-3-hydroxy-4-(1,2,4-(1H)-triazolyl)butane.

62. The method as defined in claim 50 wherein the active ingredient is 1,1,1-trichloro-3-((4-phenyl)-phenyl)-3-hydroxy-4-(1,2,4-(1H)-triazolyl)butane.

63. The method as defined in claim 50 wherein the active ingredient is 1,1,1-trichloro-3-((4-trifluoromethyl)phenyl)-3-hydroxy-4-(1,2,4-(1H)-triazolyl)butane.

64. The method as defined in claim 50 wherein the active ingredient is 1,1,1-trifluoro-2,2-dichloro-4-(4-chlorophenyl)-4-hydroxy-5-(1,2,4-(1H)-triazolyl)pentane.

65. The method as defined in claim 50 wherein the active ingredient is 2,2-dichloro-4-(4-chlorophenyl)-4-hydroxy-5-(1,2,4-(1H)-triazolyl)pentane.

66. The method as defined in claim 50 wherein the active ingredient is 1,1,1-trichloro-3-(4-methylphenyl)-3-hydroxy-4-(1,2,4-(1H)-triazolyl)butane.

67. A method as defined in claim 49 wherein wherein R is —C(O)R$^4$.

68. The method as defined in claim 66 wherein the active ingredient is 3-acetoxy-1,1,1-trichloro-3-(4-chlorophenyl)-4-(1,2,4-(1H)-triazolyl)butane.

69. The method as defined in claim 66 wherein the active ingredient is 3-trifluoroacetoxy-1,1,1-trichloro-3-(4-chlorophenyl)-4-(1,2,4-(1H)-triazolyl)butane.

* * * * *